United States Patent [19]

Baggiolini et al.

[11] Patent Number: 4,595,776

[45] Date of Patent: Jun. 17, 1986

[54] SYNTHESIS OF 1α,25-DIHYDROXYERGOCALCIFEROL

[75] Inventors: Enrico G. Baggiolini; Andrew D. Batcho, both of North Caldwell; Alfred Boris, Parsippany; Milan R. Uskokovic, Upper Montclair, all of N.J.

[73] Assignee: Hoffmann-La Roche Inc., Nutley, N.J.

[21] Appl. No.: 682,113

[22] Filed: Dec. 17, 1984

Related U.S. Application Data

[62] Division of Ser. No. 477,059, Mar. 21, 1983, Pat. No. 4,508,651.

[51] Int. Cl.$^4$ ...................... C07F 7/04; C07C 49/633
[52] U.S. Cl. .................................... 556/436; 568/374; 568/819

[58] Field of Search ................. 568/374, 819; 556/436

[56] References Cited

U.S. PATENT DOCUMENTS 3,825,569  7/1974  Hajos et al. .......................... 568/374
3,965,117  6/1976  Hajos et al. .......................... 568/374

Primary Examiner—James H. Reamer
Attorney, Agent, or Firm—Jon S. Saxe; Bernard S. Leon; William G. Isgro

[57] ABSTRACT

The invention is directed to a process and intermediates for the preparation of 1α,25-dihydroxyergocalciferol as well as substantially pure and crystalline 1α,25-dihydroxyergocolciferol. The end-product 1α,25-dihydroxyergocalciferol is useful in the treatment of disease states which are characterized by insufficient amounts of 1α,25-dihydroxycholecalciferol.

4 Claims, No Drawings

SYNTHESIS OF 1α,25-DIHYDROXYERGOCALCIFEROL

This is a division, of application Ser. No. 477,059 filed Mar. 21, 1983 now U.S. Pat. No. 4,508,651.

BRIEF SUMMARY OF THE INVENTION

The invention relates to a process of the preparation of 1α,25-dihydroxyergocalciferol (also known as 9,10-seco(5Z, 7E, 22E)-5, 7, 10 (19), 22-ergostatetraene-1α,3β,25-triol) of the formula

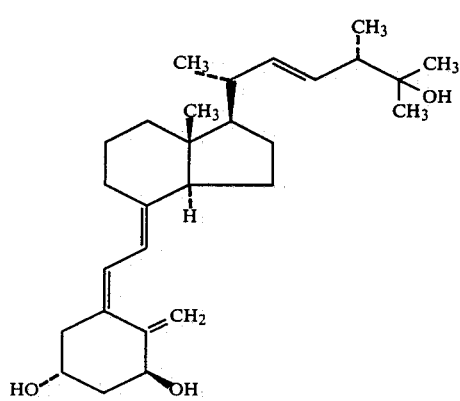

which comprises the steps of (a) reacting a compound of the formula

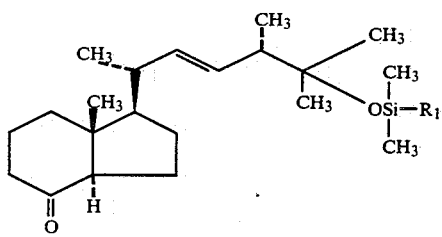

wherein $R_1$ is lower alkyl, aryl, or ar-lower alkyl, with a compound of the formula

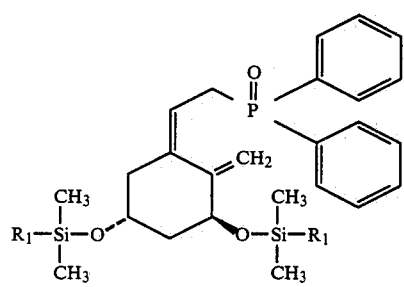

wherein $R_1$ is as previously described to yield a compound of the formula

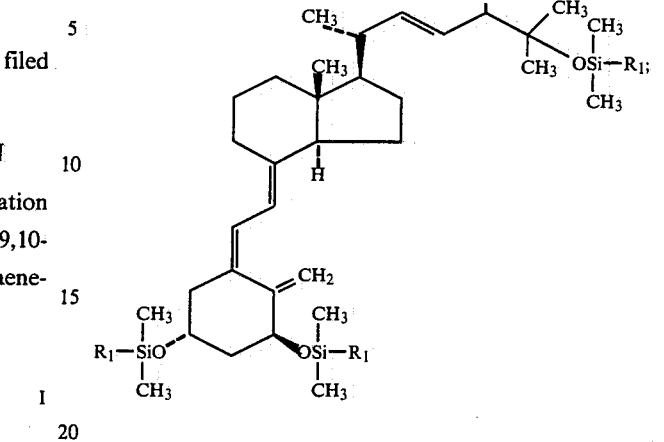

(b) removing the protecting groups from a compound of formula IV wherey there is obtained the compound of formula I.

In another aspect, the invention relates to intermediates of the formulas

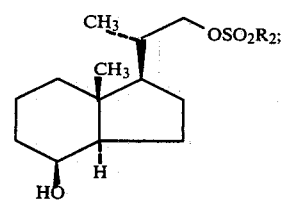

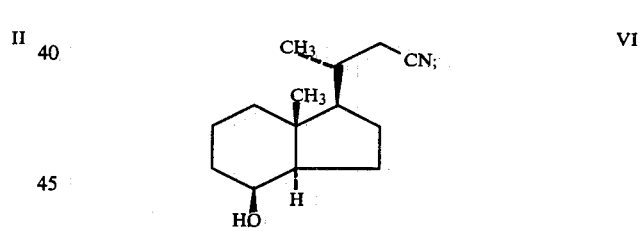

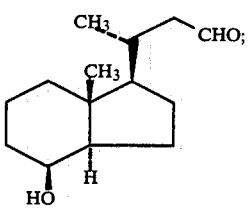

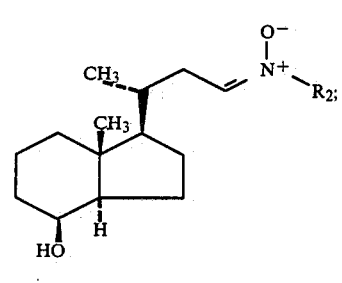

-continued

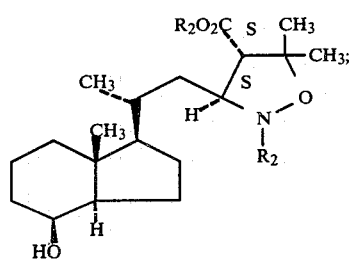

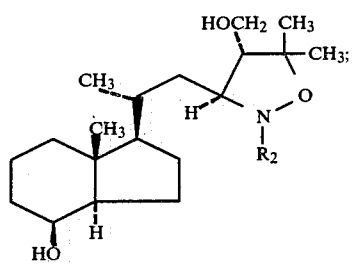

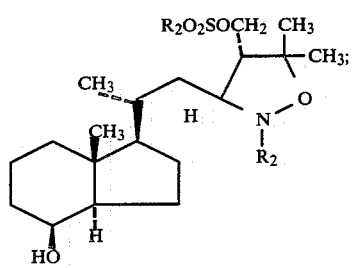

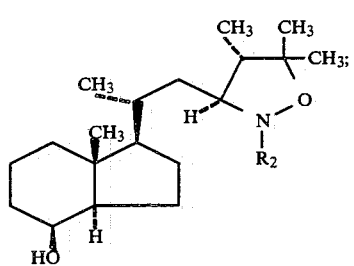

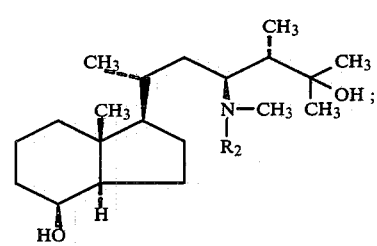

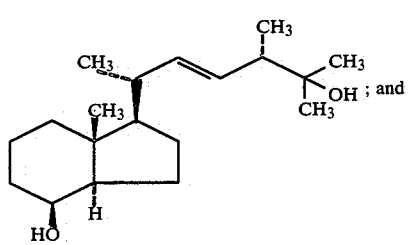

-continued

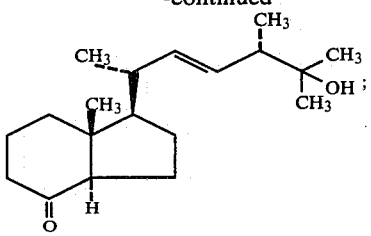

wherein above, in each occurence, $R_2$ is lower alkyl, aryl or ar-lower alkyl.

DETAILED DESCRIPTION OF THE INVENTION

As used throughout the specification and the appended claims, the term "lower alkyl" denotes an aliphatic hydrocarbon radical of from 1 to 8 carbon atoms, which may be straight- or branched-chain. Examples of "lower alkyl" are methyl, ethyl, n-propyl, 1-propyl, tert-butyl, hexyl, heptyl, octyl and the like. The term "ar-lower alkyl" denoted a lower alkyl radical which is substituted by an aryl group. Exemplary of "ar-lower alkyl" are p-tolyl, benzyl, phenylethyl, phenylpropyl and the like. The term "aryl" denotes a radical derived from an aromatic hydrocarbon which may be unsubstituted or substituted by one or more lower alkyl groups. Exemplary of aryl are phenyl and p-methyl phenyl.

In the formulas represented herein the various substituents are illustrated as joined to the nucleus by one of the following notations. A solid line ( ) indicates that a substituent is in the β-orientation, that is, above the plane of the molecule, a broken line ( ) indicates that a substituent is in the α-orientation, that is, below the plane of the molecule, and a wavy line ( ) indicates that the substituent may be in either the α or β orientation or in a mixture of compounds containing substituents in the α and/or β orientation. The Greek letter xi (ξ) in the name of an intermediate indicates that the stereochemistry of the substituent to which it refers is undefined or that, in the case of an end-product, it consists of a mixture of compounds epimeric at the designated position.

As previously mentioned, the compound of formula I is prepared by the reaction of the compound of the formula III, a known compound, with the compound of formula II, the synthesis of which is herein described.

The invention comprises a process for the preparation of the compound of the formula

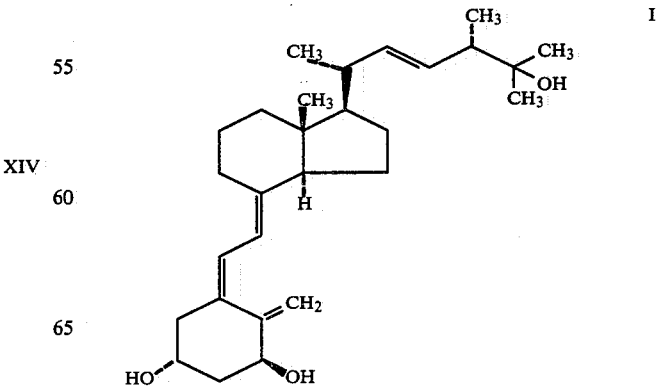

(a) reacting a compound of the formula

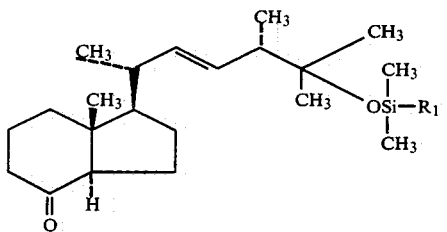

II wherein R₁ is lower alkyl, aryl or ar-lower alkyl, with the compound of the formula

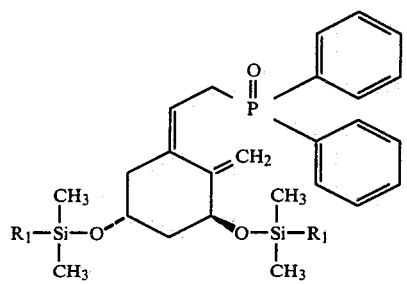

III wherein R₁ is as described above, to yield the compound of the formula

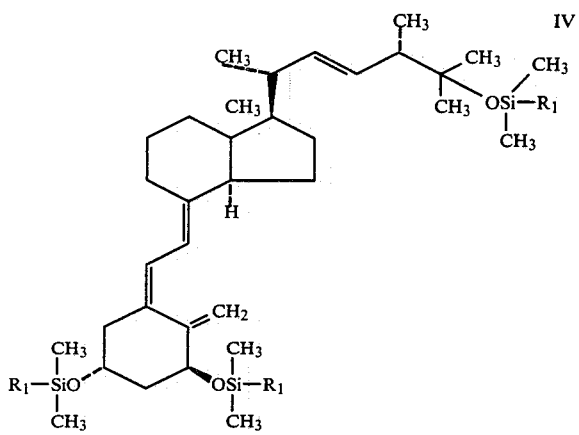

IV wherein R₁ is as described above and (b) removing the protecting groups from the compound of formula IV, whereby there is obtained the compound of formula I.

In accordance with the invention, a ketone of the formula II is reacted with a phosphine oxide of the formula III, which are known compounds or can be prepared according to known procedure, to yield a corresponding compound of formula IV. The reaction is carried out in the presence of a base in a conventional ether solvent, for example, diethyl ether, tetrahydrofuran or the like, under an inert atmosphere at a temperature in the range of from about −80° C. to about −50° C. Exemplary of suitable bases are lower alkyl lithium compounds, alkali methyl dialkyl or disilyl amides or the like. The compound of formula IV can be purified by elution chromatography on silica gel.

The compound of formula IV is converted to the compound of formula I by removal of the hydroxyl derivatizing groups utilizing a tetraalkylammonium fluoride in a suitable inert organic solvent. While any tetraalkylammonium fluoride can be used, tetrabutylammonium fluoride is preferred. Exemplary of suitable inert organic solvents are lower aliphatic hydrocarbon solvents, such as hexane, heptane and the like, aromatic hydrocarbons, such as benzene and toluene, or conventional ether solvents, such as diethyl ether, tetrahydrofuran and the like: tetrahydrofuran is preferred. The foregoing reaction is carried out at temperatures in the range of about 0° C. to about boiling point of the solvent, with room temperature being preferred.

A compound of formula II, which is a starting material in the process of the invention can be prepared as hereinafter described.

More specifically, a sulfonyloxy compound of the formula

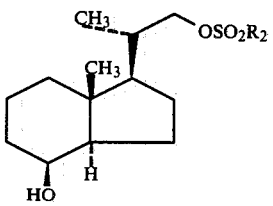

V wherein R₂ is lower alkyl, aryl or ar-lower alkyl is reacted with sodium cyanide to yield the compound of the formula

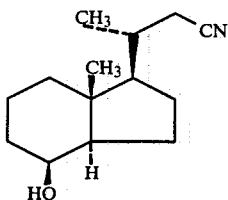

VI

Generally, it is preferred to carry out this reaction in inert organic solvents, such as acetone, acetonitrile, dimethylformamide or dimethylsulfoxide at temperature in the range of 0° C. to the boiling point of the solvent.

In the next step, the compound of formula VI is reduced by treatment with a hydride reducing agent in an inert organic solvent to yield the aldehyde of the formula

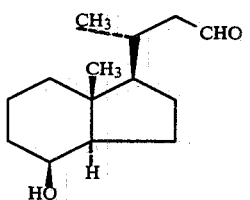

VII

Exemplary of suitable hydride reducing agents are diisobutylaluminum hydride, lithium aluminum hydride and the like: diisobutylaluminum hydride is especially preferred. Exemplary of suitable inert organic solvents are lower aliphatic hydrocarbon solvents, such as hexane, heptane, octane and the like; conventional ether solvents, such as diethyl ether, tetrahydrofuran and the like; aromatic hydrocarbons, such as benzene, toluene and the like; or lower alkyl halide solvents, such as methylene chloride, chloroform, carbon tetrachloride and the like. The foregoing reaction is carried out at a temperature in the range of about −70° C. to about 80° C.; a temperature in the range of about 0° C. to about room temperature is preferred.

In the next step, the compound of formula VII is reacted with an alkyl, aryl or ar-lower alkyl hydroxylamine hydrochloride in the presence of a tertiary amine at a temperature in the range of about 0° C. to about 80° C., room temperature is preferred, to yield a compound of the formula

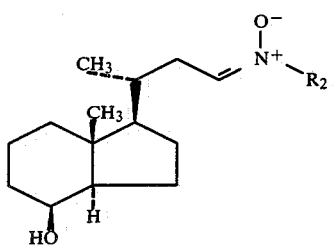
VIII wherein $R_2$ is lower alkyl, aryl or ar-lower alkyl.

Exemplary of suitable tertiary amine are tri-lower alkylamines, pyridine and the like. Exemplary of suitable solvents are lower alkyl alcohols, such as methanol, ethanol, t-butanol, isopropanol, and the like; and conventional ether solvents, such as diethyl ether, tetrahydrofuran and the like.

In the next step, a compound of formula VIII is cyclized by a reaction with an alkyl, aryl or ar-lower alkyl 3,3-dimethylacrylate in an inert organic solvent at temperature in the range of about room temperature to about boiling point of the solvent, a 140° temperature is preferred, to yield a compound of the formula

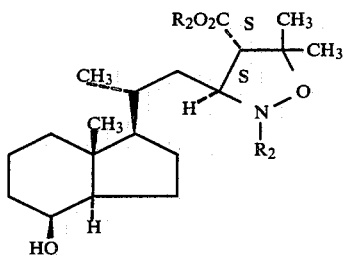
IX wherein $R_2$ is lower alkyl, aryl or ar-lower alkyl.

Exemplary of suitable 3,3-dimethylacrylates are methyl, ethyl, or benzyl 3,3-dimethylacrylate, and the like. Exemplary of suitable solvents are lower aliphatic hydrocarbon solvents, such as hexane, heptane, octane, and the like; lower alkyl alcohols, such as methanol, ethanol, propanol, and the like; conventional ether solvents, such as diethyl ether, tetrahydrofuran and the like; and aromatic hydrocarbon solvents, such as benzene, toluene, xylene and the like.

In the next step, a compound of formula IX is reduced by reacting with a hydride reducing agent in an inert organic solvent to yield a compound of the formula

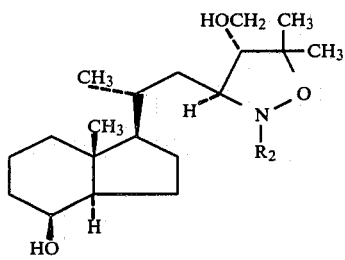
X wherein $R_2$ is lower alkyl, aryl or ar-lower alkyl.

Exemplary of suitable hydride reducing agents are diisobutylaluminum hydride, lithium aluminum hydride and the like; lithium aluminum hydride is especially preferred. Exemplary of suitable inert organic solvents are lower aliphatic hydrocarbon solvents, such as hexane, heptane, octane and the like; conventional ether solvents, such as diethyl ether, tetrahydrofuran and the like; aromatic hydrocarbons, such as benzene, toluene and the like; or lower alkyl halide solvents, such as methylene chloride, chloroform, carbon tetrachloride and the like. The foregoing reaction is carried out at a temperature in the range of about −70° C. to about 80° C.; room temperature is preferred.

In the next step a compound of the formula X is reacted with a suitable sulfonating agent in a basic organic solvent to yield a compound of the formula

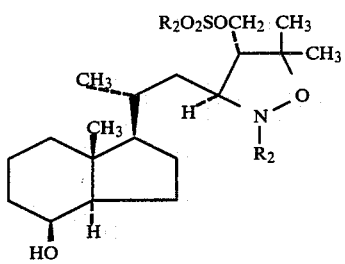
XI wherein $R_2$ is lower alkyl, aryl or ar-lower alkyl.

Exemplary of suitable sulfonating agents are p-toluenesulfonyl chloride, methane-sulfonyl chloride and the like; p-toluenesulfonyl chloride is especially preferred. Exemplary of basic organic solvents are lower tertiary alkyl amines, pyridine, substituted pyridine and the like. The foregoing reaction is carried out at a temperature in the range of about 0° C. to about 80° C.; room temperature is preferred.

In the next step, a compound of formula XI is reduced by reaction with a hydride reducing agent in an inert organic solvent to yield a compound of the formula

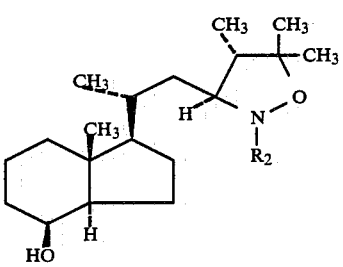
XII wherein $R_2$ is lower alkyl, aryl or ar-lower alkyl.

Exemplary of suitable hydride reducing agents are diisobutylaluminum hydride, lithium aluminum hydride and the like; lithium aluminum hydride is especially preferred. Exemplary of suitable inert organic solvents are lower aliphatic hydrocarbon solvents, such as hexane, heptane, octane and the like; conventional ether solvents, such as diethyl ether, tetrahydrofuran and the like; aromatic hydrocarbons, such as benzene, toluene and the like; or lower alkyl halide solvents, such as methylene chloride, chloroform, carbon tetrachloride and the like. The foregoing reaction is carried out at a temperature in the range of about −70° C. to about 80° C.; room temperature is preferred.

In the next step, a compound of formula XII is converted to a compound of formula

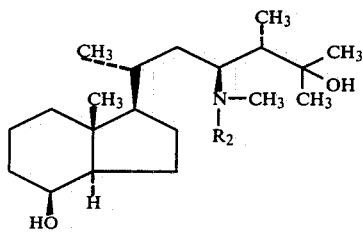

XIII wherein $R_2$ is a lower alkyl, aryl or ar-lower alkyl, by treating a compound of formula XII with methyl iodide in dry toluene, at a temperature in the range of about room temperature to 80° C.; 60° C. is preferred. The foregoing is followed by reduction with zinc dust in aqueous acetic acid at room temperature.

In the next step, a compound of the formula XIII is converted to the compound of the formula

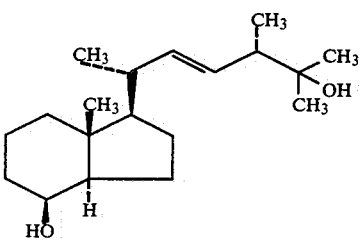

XIV by an elimination process which comprises treating a compound of formula XIII first with methyl iodide in toluene at a temperature in the range of about room temperature to 100° C.; 70° C. is preferred. The foregoing is followed by treatment with potassium t-butoxide in t-butyl alcohol at reflux temperature.

In the next step, a compound of the formula XIV is oxidized to the ketone of the formula

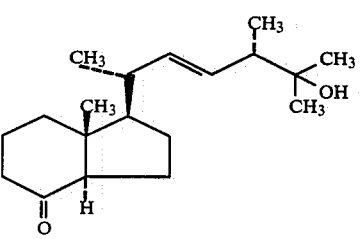

XV by treating the compound of the formula XIV with pyridinium chlorochromate in a suitable inert organic solvent. Exemplary of suitable inert organic solvents are lower aliphatic hydrocarbon solvents, such as hexane, heptane, octane and the like; aromatic hydrocarbons, such as benzene, toluene and the like; or lower alkyl halide solvents, such as methylene chloride, chloroform, carbon tetrachloride and the like. The foregoing reaction is carried out at a temperature in the range of about 0° C. to the boiling point of the solvent; room temperature is preferred.

In the next step, the hydroxyl group of the compound of formula XV is protected by a suitable silylating agent in a suitable inert organic solvent to yield a corresponding compound of the formula

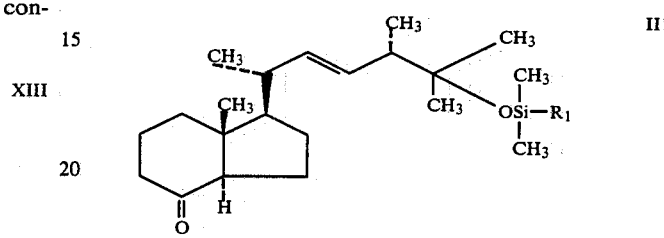

II wherein $R_1$ is lower alkyl, aryl, or ar-lower alkyl.

Exemplary of suitable silylating agents are N-(trimethylsilyl)imidazole, trimethylsilyl chloride, t-butyldimethylsilyl chloride and the like; N-(trimethylsilyl)imidazole is especially preferred. Exemplary of suitable inert organic solvents are lower aliphatic hydrocarbon solvents, such as hexane, heptane, octane and the like; conventional ether solvents, such as diethyl ether, tetrahydrofuran and the like; aromatic hydrocarbons, such as benzene, toluene and the like; or lower alkyl halide solvents, such as methylene chloride, chloroform, carbon tetrachloride and the like. The foregoing reaction is carried out at a temperature in the range of about −70° C. to about 80° C., room temperature is preferred.

The 1α,25-dihydroxyergocalciferol of formula I is useful in the treatment of disease states in warm-blooded animals which are characterized by insufficient amounts or levels of 1α,25-dihydroxycholecalciferol. More particularly, the 1α,25-dihydroxyergocalciferol of formula I is useful in the treatment of osteoporosis and osteodystrophy. The useful activity of the 1α,25-dihydroxyergocalciferol of formula I can be demonstrated in the test procedures hereinafter described.

Antirachitogenic Activity of 1α,25-Dihydroxyergocalciferol

Antirachitogenic activity was measured according to the published procedure by A. Boris, J. F. Hurley and T. Trmal, The Journal of Nutrition, 107, (2), 194 (1977). 1α,25-Dihydroxyergocalciferol was administered orally in propylene glycol for 21 consecutive days to chicks which were fed a Vitamin D-deficient diet and housed under ultraviolet-free lighting. Each group had 9–10 chicks. The following results were obtained:

TABLE I

| Dose ng/chick/day, p.o. | Mean Tibia Ash ± S.E. (mg) |
|---|---|
| 0 | 88.0 ± 6.1 — |
| 30 | 103.4 ± 3.5 $p < .05$ |
| 100 | 130.0 ± 6.3 $p < .001$ |
| 300 | 141.3 ± 5.1 $p < .001$ |

EHDP Induced Mineralization Block Inhibition Activity of 1α,25-Dihydroxyergocalciferol The test was done according to the known procedure by A. Boris, J. F. Hurley, T. Trmal, J. P. Mallon and D. S. Matuszewski, The Journal of Nutrition, 108 (12), 1899 (1978). 1α,25-Dihydroxyergocalciferol was administered orally for 10 consecutive days to rats which received concurrent subcutaneous injections of ethane-1-hydroxy-1,1-diphosphate (EHDP). Each group had 9–10 rats. The following results were obtained:

TABLE II

| Dose ng/rat/day, p.o. | Mean ± S.E. Tibial Epiphyseal Plate Width (μ) 1α,25-Dihydroxy-ergocalciferol |
|---|---|
| 0 | 1497 ± 20 |
| 1 | 1471 ± 34 NS |
| 3 | 1409 ± 29 p < .05 |
| 10 | 1233 ± 29 p < .001 |
| 30 | 933 ± 15 p. < .001 |

Vehicle Controls 441 ± 5

The compound of formula I can be administered at an oral dose in the range of from about 1 to about 5 micrograms per day for the treatment of osteoporosis. A preferred dosage for the treatment of the above disease state is about 2 micrograms per day. The compound of formula I can be administered at an oral dose in the range of from 1 to about 5 micrograms per day also for the treatment of osteodystrophy. A preferred dosage for the treatment of the above disease state is about 2 micrograms per day. The compound of formula I can be administered, as required, orally, subcutaneously, intramuscularly, intravenously, or intraperitoneally.

The compound of formula I can be formulated into compositions such as tablets, capsules, and the like, or elixirs for oral administration, or in sterile solutions or suspension for parenteral administration. About 1–5 micrograms of the compound of formula I is compounded with a pharmaceutically acceptable vehicle, carrier, excipient, binder, preservative, stabilizer, flavor, and the like, in unit dosages as called for by accepted pharmaceutical practice. The amount of active substance in the foregoing compositions or preparations is in the range previously indicated.

Illustrative of the adjuvants which may be incorporated into capsules, and the like are the following: a binder, such as gum tragacanth, acacia, corn starch, or gelatin; an excipient, such as dicalcium phosphate; a disintegrating agent, such as corn starch, potato starch, algenic acid, and the like; a lubricant, such as magnesium stearate, a sweetening agent, such as sucrose, lactose, or saccharin; a flavoring agent, such as peppermint, oil of wintergreen or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and as flavoring, such as cherry or orange flavor.

Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottenseed oil, and the like, or a synthetic fatty vehicle, such as ethyl oleate or the like. Buffers, preservatives, antioxidants and the like can be incorporated as required.

The Examples which follow further illustrate the invention. All temperatures are in degrees Centigrade unless otherwise stated.

EXAMPLE 1

Preparation of
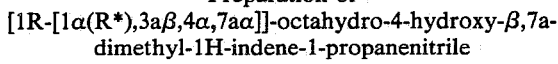
[1R-[1α(R*),3aβ,4α,7aα]]-octahydro-4-hydroxy-β,7a-dimethyl-1H-indene-1-propanenitrile To a solution of 6.75 g (137.5 mmol) of sodium cyanide in 175 ml of dry dimethylsulfoxide (dist. from calcium hydride) under an argon atmosphere was added a solution of 42.0 g (114.6 mmol) of [1R-[1α(S*),3aβ,4α,7aα]]-octahydro-4-hydroxy-β,7a-dimethyl-1H-indene-1-ethanol α-(4-methylbenzenesulfonate) in 100 mL of dry dimethylsulfoxide. The resulting solution was heated at 90° for 2¼ hours. (TLC: methylene chloride-ethyl acetate, 9:1), then poured into 2.5 L of brine and extracted with 6×500 mL of ether. Each extract was washed with 500 mL of brine. The combined organic phases were dried (sodium sulfate) and evaporated to give 25.60 g of crude product. Purification by LC (45×500 mm column of silica gel; hexane-ethyl acetate, 9:1) gave 22.26 g (80% yield) of [1R-[1α(R*), 3aβ,4α,7aα]]-octahydro-4-hydroxy-β,7a-dimethyl-1H-indene-1-propanenitrile. An anlytical sample was obtained from ether-pet. ether as a crystalline solid, mp 90.5°–91.5° C.; $[α]_D^{25}$ +46.66 (c. 0.6986, chloroform).

EXAMPLE 2

Preparation of
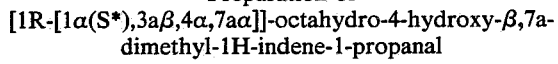
[1R-[1α(S*),3aβ,4α,7aα]]-octahydro-4-hydroxy-β,7a-dimethyl-1H-indene-1-propanal To a solution of 11.55 g (52.18 mmol) of [1B-[1α(R*)-,3aβ,4α,7aα]]-octahydro-4-hydroxy-β,7a-dimethyl-1H-indene-1-propanenitrile in 300 ml of dry toluene (4 Å molecular sieves) at 0° was added over 10 minutes 73 mL (109.6 mmol) of 1.5 M diisobutylaluminum hydride in toluene. Stirring was continued for 1 hour during which time a heavy gel formed. The reaction was quenched by cautious addition of 2.0 L of cold 2N hydrochloric acid (ice bath). Vigorous stirring continued for 1.5 hours and 560 mL of ether was added. A blanket of argon was maintained furing the extraction. Phases were separated and the aqueous phase re-extracted with 3×500 mL of ether. The combined organic layers were dried (sodium sulfate) to give 12.99 g of crude [1R,[1α(S*),3aβ,4α,7aα]]-octahydro-4-hydroxy-β,7a-dimethyl-1H-indene-1-propanal.

EXAMPLE 3

Preparation of
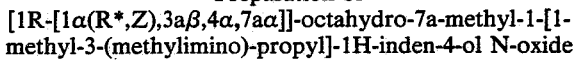
[1R-[1α(R*,Z),3aβ,4α,7aα]]-octahydro-7a-methyl-1-[1-methyl-3-(methylimino)-propyl]-1H-inden-4-ol N-oxide To a solution of 3.81 g of crude [1R,[1α(S*),3aβ,4α,7aα]]-octahydro-4-hydroxy-β,7a-dimethyl-1H-indene-1-propanal in 100 mL of dry methylene chloride was added 1.56 g (18.7 mmol) of N-methylhydroxylamine hydrochloride. The suspension was stirred ¼ hour at room temperature, then 3.20 mL (23.2 mmol) of triethylamine was added. The solution was stirred for 19 hours at room temperature, then extracted with 2×50 mL of 5% sodium bicarbonate. The organic phase was dried (sodium sulfate) and evaporated to give 3.78 g (88% yield) of [1R-[1α(R*,Z),3aβ,4α,7aα]]-octahydro- 7a-methyl-1-[1-methyl-3-(methylimino)propyl]-1H-inden-4-ol N-oxide. An analytical sample was obtained as crystals from ethyl acetate; mp 145°–146°; $[\alpha]_D^{25} +41.45°$ (c 0.808, chloroform).

EXAMPLE 4

Preparation of [3S-[3β,4α,3-[(2R*),1R*((1β,3aα,4β,7aβ)]]]-3-[2-(octahydro-4-hydroxy-7a-methyl-1H-inden-1-yl)propyl]-2,5,5-trimethyl-4-isoxazolidinecarboxylic acid methyl ester A solution of 7.50 g (29.6 mmol) of [1R-[1α(R*,Z)-,3aβ,4α,7aα]]-octahydro-7-a-methyl-1-[1-methyl-3-(methylimino)propyl]-1H-inden-4-ol N-oxide and 10.13 g (89 mmol) of methyl 3,3-dimethylacrylate in 75 ml of xylenes (purified by percolation through a silica gel column followed by distillation) was heated under a nitrogen atmosphere in an oil bath at 140° for 15 hours. Evaporation under reduced pressure on a rotary evaporator gave 11.6 g of crude product. Chromatography on 40–60 mesh silica gel (0.5 m × 45 mm column) at 60 psi with 3:1, methylene chloride-ethyl acetate as the eluent gave, on combining fractions according to tlc ($R_f = 0.45$, methylene chloride-ethyl acetate, 2:1), 5.36 g of impure product. Rechromatography as above using 5:1, methylene chloride-ethyl acetate afforded 4.5 g (41% yield) of pure [3S-[3β,4α,3-[(2R*),1R*(1β,3aα,4β,7aβ)]]]-3-[2-(octahydro-4-hydroxy-7-a-methyl-1-H-inden-1-yl)propyl]-2,5,5-trimethyl-4-isoxazolidinecarboxylic acid methyl ester. An analytical sample had mp 80°–81° (from hexanes), $[\alpha]_D^{25} +102.6$ (c 1.05, chloroform).

EXAMPLE 5

Preparation of [3S-[3β,4α,3-[(2R*),1R*(1β,3aα,4β,7aβ)]]]-3-[2-(octahydro-4-hydroxy-7a-methyl-1H-inden-1-yl)propyl]-2,5,5-trimethyl-4-isoxazolidinemethanol To a solution of 3.0 g (8.2 mmol) of [3S-[3β,4α,3-[(2R*),1R*(1β,3aα,4β,7aβ)]]]-3-[2-octahydro-4-hydroxy-7a-methyl-1H-inden-1-yl)propyl]-2,5,5-trimethyl-4-isoxazolidinecarboxylic acid methyl ester in 100 mL of dry tetrahydrofuran under an argon atmosphere was added portionwise 930 mg (24.5 mmol) of lithium aluminum hydride over 10 minutes. After stirring for 3.5 hours at room temperature, the suspension was cooled in an ice bath and 1.0 mL of water was added dropwise followed by 1.5 mL of 1N sodium hydroxide. After 15 minutes, the granular suspension was filtered (glass fiber paper) and the filter cake washed with 2 × 100 mL of ether. The combined filtrates were evaporated under reduced pressure to give 2.85 g of residue. Chromatography on 40–60 mesh silica gel (0.3 m × 25 mm column) with ethyl acetate as the eluent afforded 2.49 g (90% yield) of [3S-[3β,4α,3-[(2R*),1R*(1β,3aα,4β,7aβ)]]]-3-[2-(octahydro-4-hydroxy-7a-methyl-1H-inden-1-yl)propyl]-2,5,5-trimethyl-4-isoxazolidinemethanol. An analytical sample had mp 153° (acetonitrile), $[\alpha]_D^{25} +106.4$ (c 1.07, chloroform).

EXAMPLE 6

Preparation of [1R-[1α(R*),3aβ,4α,7aα,(3S*,4S*)]]-octahydro-7a-methyl-1-[1-methyl-2-[4-[[[(4-methylphenyl)sulfonyl]oxy]methyl]-2,5,5-trimethyl-3-isoxazolidinyl]ethyl]-1-inden-4-ol To a stirred solution of 2.49 g (7.33 mmol) of [3S-[3β,4α,3-[(2R*),1R*(1β,3aα,4β,7aβ)]]]-3-[2-octahydro-4-hydroxy-7a-methyl-1H-inden-1-yl)propyl]-2,5,5-trimethyl-4-isoxazolidinemethanol in 75 ml of dry pyridine under argon atmosphere cooled in an ice bath to 5° was added portionwise 2.10 g (11.0 mmol) of recrystallized p-toluenesulfonyl chloride over 10 minutes. The bath was removed and the reaction mixture allowed to stir at room temperature for 48 hours, then it was cooled to 5°, and 5.0 ml of water was added. After 30 minutes the reaction mixture was poured into 2 L of cold 2N sulfuric acid, and then extracted with 3 × 150 mL of methylene chloride which was back-washed with 50 mL of 10% sodium bicarbonate. The combined methylene chloride phases were dried(sodium sulfate), filtered, and evaporated to give 3.28 g (91%) of [1R--[1α(R*),3aβ,4α,7aα,(3S*,4S*)]]-octahydro-7a-methyl-1-[1-methyl-2-[4-[[[(4-methylphenyl)sulfonyl]oxy]methyl]-2,5,5-trimethyl-3-isoxazolidinyl]-ethyl]-1H-inden-4-ol. An analytical sample of the hydrate had mp 114°–115° (from hexanes) $[\alpha]_D^{25} +53.3$ (c 0.994, chloroform).

EXAMPLE 7

Preparation of [1R-[1α(R*),3aβ,4α,7aα,(3S*,4S*)]]-octahydro-7a-methyl-1-[1-methyl-2-(2,4,5,5-tetramethyl-3-isoxazolidinyl)ethyl]-1H-inden-4-ol To a stirred suspension of 3.28 g (6.65 mmol) of [1R-[1α(R*),3aβ,4α,7aα(3S*, 4S*)]]-octahydro-7a-methyl-1-[1-methyl-2-[4-[[[(4-methylphenyl)sulfonyl]oxy]methyl]-2,5,5-trimethyl-3-isoxazolidinyl]ethyl]-1H-inden-4-ol in 100 mL of dry tetrahydrofuran under an argon atmosphere was added portionwise 756 mg (19.9 mmol) of lithium aluminum hydride over 10 minutes. The suspension was heated at reflux for 1 hour, left standing at room temperature overnight, then cooled in an ice bath. After the addition of 1.0 mL of water followed by 1.5 mL of 1N sodium hydroxide, the suspension was stirred for 30 minutes, then filtered (glass fiber paper). The filter cake was washed with 2 × 100 mL of ether and the combined filtrates evaporated to give 2.48 g of residue. Chromatography on 40–60 mesh silica gel (0.5 m × 25 mm column) at 60 psi using 1:1 hexanes-ethyl acetate as eluent afforded 1.90 g of [1R-[1α(R*),3aβ,4α,7aα,(3S*, 4S*)]]-octahydro-7a-methyl-1-[1-methyl-2-(2,4,5,5-tetramethyl-3-isoxazolidinyl)ethyl]-1H-inden-4-ol, as a colorless oil.

EXAMPLE 8

Preparation of [1R-[1α(R*,S*,S*),3aβ,4α,7aα]]-octahydro-γ-(dimethylamino)-4-hydroxy-α,α,β,ε,7a-pentamethyl-1H-indene-1-pentanol A solution of 1.556 g (4.8 mmol) of [1R-[1α(R*),3aβ,4α,7aα,(3S*,4S*)]]-octahydro-7a-methyl-1-[1-methyl-2-(2,4,5,5-tetramethyl-3-isoxazolidinyl)ethyl]-1-inden-4-ol and 0.5 mL (1.0 g, 7.2 mmol) of freshly distilled methyl iodide in 75 mL of dry toluene was heated in a 60° oil bath under argon atmosphere for 17 hours. The suspension was evaporated under reduced pressure and the residue was treated at room temperature, with 100 mL of aqueous acetic acid (1:1, v/v) and 1.72 g (26.3 mmol) of zinc dust for 2.5 hours. After evaporation under reduced pressure, the residue was partitioned between 100 mL of ethyl acetate and 25 mL of 1.5N ammonium hydroxide followed by 25 mL of brine wash. The aqueous phases were extracted with 3×50 mL of ethyl acetate in a counter-current manner. The ethyl acetate phases were combined, dried (sodium sulfate), filtered, and evaporated to give 1.554 g of crude product. Chromatography on 40-60 mesh silica gel (0.5 m×25 mm column) afforded, on elution with ethyl acetate-triethylamine (95:5), 1.46 g (89% yield) of pure [1R-[1α(R*,S*,S*),3aβ,4α,7aα]]-octahydro-γ-(dimethylamino)-4-hydroxy-α,α,β,ε, 7a-pentamethyl-1H-indene-1-pentanol. An analytical sample had mp 180°-181° (from ethyl acetate), $[\alpha]_D25 +4.79°$ (c 1.044, chloroform).

EXAMPLE 9

Preparation of
[1R-[(1α-(R*),2E,4S*,3aβ,4α,7aα]]-octahydro-1-(5-hydroxy-1,4,5-trimethyl-2-hexenyl)-7a-methyl-1H-inden-4-ol A solution of 679 mg (2.0 mmol) of [1R-[1α-(R*,S*,S*),3aβ,4α,7aα]]-octahydro-γ-(dimethylamino)-4-hydroxy-α,α,β,ε,7a-pentamethyl-1-H-indene-1-pentanol and 0.35 mL (850 mg, 6.0 mmol) of freshly distilled iodide in 10 mL of toluene (dried over 4A molecular sieves) was heated at 70° under an argon atmosphere for 20 hours. After evaporation under reduced pressure, the residue was dissolved in 25 mL of distilled t-butyl alcohol under an argon atmosphere and 450 mg (4.0 mmol) of potassium t-butoxide was added. The suspension was heated at reflux for 5 hours, cooled to room temperature, and, after the addition of 0.5 mL of water, was evaporated to dryness. The residue was triturated with 2×25 mL of methylene chloride to give 0.71 g of crude product. Chromatography on 40-60 mesh silica gel (0.3 m×25 mm column) at 42 psi, using 3:1 hexanes-ethyl acetate as the eluent and combining fractions according to tlc ($R_f$ 0.21, hexanes-ethyl acetate, 3:1), afforded 0.460 mg (78% yield) of [1R-[(1α-(R*),2E,4S*,3aβ,4α,7aα]]-octahydro-1-(5-hydroxy-1,4,5-trimethyl-2-hexenyl)-7a-methyl-1H-inden-4-ol. An analytical sample had mp 103°-104° (from hexanes), $[\alpha]_D25 +2.01°$ (c 1.046, chloroform).

EXAMPLE 10

Preparation of
[1R-[1α(1R*,2E,4S*),3aβ,7aα]]-octahydro-1-(5-hydroxy-1,4,5-trimethyl-2-hexenyl)-7a-methyl-4H-inden-4-one A solution of 200.0 mg (0.684 mmol) of [1R-[1α-(1R*,2E,4S*),3aβ,4α,7aα]]-octahydro-1-(5-hydroxy-1,4,5-trimethyl-2-hexenyl)-7a-methyl-1H-inden-4-ol in 3 mL of dry methylene chloride was rapidly added to a suspension of 440.0 mg (2.041 mmol) of pyridinium chlorochromate in 12 mL of dry methylene chloride and the resulting mixture stirred at room temperature for 3 hours. It was then diluted with 40 mL of diethyl ether, filtered through diatomaceous earth and the solvent evaporated. The residue was purified by fast filtration through a short silica gel column, eluted with hexane-ethyl acetate (3:1) to give 185.0 mg (93% yield) of the desired [1R-[1α-(1R*,2E,4S*), 3aβ,7aα]]-octahydro-1-(5-hydroxy-1,4,5-trimethyl-2-hexenyl)7a-methyl-4H-inden-4-one, which was crystallized from hexane-methylene chloride; mp 101°-102° C.; $[\alpha]_D25 -6.89°$ (c 0.5, ethyl alcohol).

EXAMPLE 11

Preparation of
[1R-[1α-(1R*,2E,4S*),3aβ,7aα]]-octahydro-1-(1,4,5-trimethyl-5-trimethylsilyloxy-2-hexenyl)-7a-methyl-4H-inden-4-one A solution of 200.0 mg (0.679 mmol) of [1R-[1α-(1R*,2E,4S*),3aβ,7aα]]-octahydro-1-(5-hydroxy-1,4,5-trimethyl-2-hexenyl)-7a-methyl-4H-inden-4-one in 10 mL of dry methylene chloride was treated with 0.4 mL (2.726 mmol) of N-(trimethylsilyl)imidazole and the resulting mixture stirred at room temperature, under argon, for 18 hours. It was then treated with 1 mL of water, stirred for an additional 30 minutes then diluted with methylene chloride. The organic phase was separated, washed with water and brine, dried and evaporated to dryness. The residue obtained was purified by rapid filtration through a short silica gel column, eluted with hexane-ethyl acetate (5:1) to give 214.0 mg (84% yield) of pure [1R-[1α-(1R*,2E,4S*),3aβ,7aα]]-octahydro-1-(1,4,5-trimethyl-5-trimethylsilyloxy-2-hexenyl)-7a-methyl-4H-inden-4-one, as a thick, colorless oil.

EXAMPLE 12

Preparation of
9,10-Seco(5Z,7E,22E)-5,7,10(19),22-ergostatetraene-1α,3β,25-triol(1α,25-dihydroxyergocaliferol)

A solution of 360.0 mg (0.617 mmol) of [3S-(3α,5β,Z)]-2-[2-methylene-3,5-bis-[(1,1-dimethylethylethyl)dimethylsilyloxy]cyclohexyliden]ethyldiphenyl phosphine oxide in 12 mL of dry tetrahydrofuran was cooled to −78° C. and treated dropwise, under argon, with 0.390 mL (0.604 mmol) of a 1.55M solution of N-butyllithium in hexane. After stirring for 5 minutes a solution of 150.0 mg (0.411 mmol) of [1R-[1α-(1R*,2E,4S*),3aβ,7aα]]-octahydro-1-(1,4,5-trimethyl-5-trimethylsilyloxy-2-hexenyl)-7a-methyl-4H-inden-4-one in 3 mL of dry tetrahydrofuran was slowly added and the resulting mixture stirred at −78° C. for 1.5 hours. It was then treated with 5 mL of a 1:1 mixture of 1N sodium bicarbonate and 2N potassium sodium tartrate, allowed to come to room temperature, diluted with water and extracted with 3×80 mL of ethyl acetate. The combined organic extracts were washed with brine, dried and evaporated. The residue was purified by chromatography on silica gel, eluting with hexane-ethyl acetate (5:1) to give 261.0 mg of a colorless, thick oil. This was dissolved in 6 mL of dry tetrahydrofuran, combined with 1.8 mL (1.8 mmol) of a 1M solution of tetrabutylammonium fluoride in tetrahydrofuran and stirred at room temperature, under argon, for 23 hours. The solvent was then removed in vacuo and the residue dissolved in 100 mL of ethyl acetate, washed with 5×30 mL of water, then with 50 mL of brine, dried and evaporated. The residue was purified by rapid filtration through a small silica gel column, eluted with ethyl acetate to give 140.0 mg (80%) of pure 9,10-seco(5Z,7E,22E)-5,7,10(19),22-ergostatetraene-1α,3β,25-triol(-1α,25-dihydroxyergocalciferol); mp 165°-167° C.; $[\alpha]_D25 +47.2°$ (c 0.2, ethyl alcohol).

EXAMPLE 13

| Item | Ingredients | mg/capsule | | |
|---|---|---|---|---|
| 1. | 1α,25-dihydroxy-ergocalciferol | 0.001 | 0.0025 | 0.005 |
| 2. | polyethylene glycol 400 (PEG 400) | 200.00000 | 200.0000 | 200.0000 |
| 3. | butylated hydroxy anisole (BHA) | 0.10000 | 0.1000 | 0.1000 |
| 4. | ascorbyl palmitate | 1.00000 | 1.0000 | 1.0000 |

Procedure:
Dissolve items 1, 3 and 4 in item 2, under a blanket of nitrogen and encapsulate.

We claim:

1. The compound, [1R-[(1α(R*),2E,4S*,3aβ,4α,-7aα]]-octahydro-1-(5-hydroxy-1,4,5-trimethyl-2-hexenyl)-7a-methyl-1H-inden-4-ol, of the formula

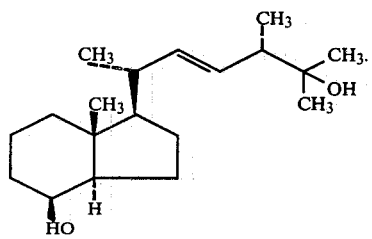

XIV

2. The compound, [1R-[1α(1R*,2E,4S*),3aβ,7aα]]-octahydro-1-(5-hydroxy-1,4,5-trimethyl-2-hexenyl)-7a-methyl-4H-inden-4-one, of the formula

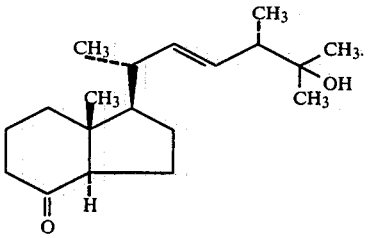

XV

3. A compound of the formula

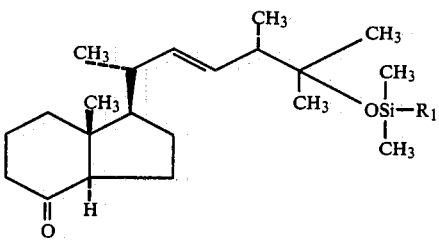

II wherein $R_1$ is lower alkyl, or phenyl, benzyl, phenylethyl or phenylpropyl which optionally may be substituted by one or more lower alkyl groups.

4. The compound in accordance with claim 3, wherein $R_1$ is methyl, that is, [1R-[1α(1R*,2E,4S*)-,3aβ,7aα]]-octahydro-1-(1,4,5-trimethyl-5-trimethylsilyloxy-2-hexenyl)-7a-methyl-4H-inden-4-one.

* * * * *